(12) United States Patent
Briscoe et al.

(10) Patent No.: US 10,691,827 B2
(45) Date of Patent: Jun. 23, 2020

(54) COGNITIVE SYSTEMS FOR ALLOCATING MEDICAL DATA ACCESS PERMISSIONS USING HISTORICAL CORRELATIONS

(71) Applicant: International Business Machines Corporation, Armonk, NY (US)

(72) Inventors: Iyanna Briscoe, Beckenham (GB); Steven L. Harrington, Austin, TX (US); Tyler N. King, Wappingers Falls, NY (US); Newton J. Piccone, Durham, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 204 days.

(21) Appl. No.: 15/844,869

(22) Filed: Dec. 18, 2017

(65) Prior Publication Data
US 2019/0188410 A1 Jun. 20, 2019

(51) Int. Cl.
*G06F 21/62* (2013.01)
*G16H 50/70* (2018.01)
(Continued)

(52) U.S. Cl.
CPC ........ *G06F 21/6245* (2013.01); *G06F 16/243* (2019.01); *G06F 21/604* (2013.01);
(Continued)

(58) Field of Classification Search
CPC .... G06F 21/6245; G06F 16/243; G06F 17/27; G06F 21/604; G06F 11/108; G16H 50/70; G06N 3/08
See application file for complete search history.

(56) References Cited

U.S. PATENT DOCUMENTS 8,606,593 B1 * 12/2013 Green, III ............. G06Q 10/06
705/2
8,924,233 B2 * 12/2014 Backhaus ............. G06Q 10/06
705/2
(Continued)

OTHER PUBLICATIONS

M S Saranya, et al., Jan. 19-21, 2017, Intelligent medical data storage system using machine learning approach, 2016 Eighth International Conference on Advanced Computing (ICoAC), pp. 191-195.*
(Continued)

*Primary Examiner* — Farid Homayounmehr
*Assistant Examiner* — Raied A Salman
(74) *Attorney, Agent, or Firm* — Cantor Colburn LLP; William Kinnaman (57) ABSTRACT

Embodiments of the present invention provide a computer-implemented method for allocating medical data access permissions using historical correlations. The method receives a request for medical research data from a user. The method executes natural language processing to interpret the received request. The method generates a database query based on a trained model to identify a medical research data set that is responsive to the request. The method queries one or more medical databases using the generated query to identify the medical research data set that is responsive to the request. The medical research data set that is identified includes the requested medical research data as well as additional medical research data that, although not requested by the user, is found to be relevant to the request based on the trained model. The method includes transmitting the medical research data set to the user.

17 Claims, 6 Drawing Sheets

(51) Int. Cl.
*G06N 3/08* (2006.01)
*G06F 21/60* (2013.01)
*G06F 16/242* (2019.01)
*G06F 40/20* (2020.01)

(52) U.S. Cl.
CPC .............. *G06F 40/20* (2020.01); *G06N 3/08* (2013.01); *G16H 50/70* (2018.01)

(56) References Cited

U.S. PATENT DOCUMENTS

| | | | | |
|---|---|---|---|---|
| 9,047,215 | B1* | 6/2015 | Chiu | H03K 19/01728 |
| 9,715,576 | B2* | 7/2017 | Hayter, II | G16H 30/20 |
| 9,953,088 | B2* | 4/2018 | Gruber | G06F 16/9535 |
| 10,242,037 | B2* | 3/2019 | Anand | G06F 16/221 |
| 10,311,364 | B2* | 6/2019 | Beechuk | G06N 5/048 |
| 2005/0203881 | A1* | 9/2005 | Sakamoto | G06F 21/552 |
| 2006/0085347 | A1* | 4/2006 | Yiachos | G06F 21/6245 |
| | | | | 705/51 |
| 2010/0262545 | A1* | 10/2010 | Herlitz | G06Q 10/00 |
| | | | | 705/51 |
| 2012/0278760 | A1 | 11/2012 | Cerny et al. | |
| 2014/0096181 | A1* | 4/2014 | Rivers | G06F 21/552 |
| | | | | 726/1 |
| 2015/0127379 | A1 | 5/2015 | Sorenson | |
| 2015/0193544 | A1* | 7/2015 | Deshpande | G06F 16/9535 |
| | | | | 707/723 |
| 2015/0326539 | A1* | 11/2015 | Sharma | H04L 9/3242 |
| | | | | 713/168 |
| 2016/0378919 | A1* | 12/2016 | McNutt | G06Q 50/24 |
| | | | | 705/3 |
| 2017/0220746 | A1* | 8/2017 | Marshall | G06F 16/00 |
| 2018/0067942 | A1* | 3/2018 | Hasegawa | G06F 16/3346 |
| 2018/0277242 | A1* | 9/2018 | Zhong | A61B 5/746 |

OTHER PUBLICATIONS

Asaph Azaria, et al., MedRec Using Blockchain for Medical Data Access and Permission Management, Aug. 2016, 2016 2nd International Conference on Open and Big Data (OBD), pp. 1-6.*
(Sergio Vincent Senese, Spring 2015, https://opus.govst.edu/cgi/viewcontent.cgi?referer=&httpsredir=1&article=1056&context=theses, Governors State University, pp. 1-64, hereinafter Senese).*
Mell et al.; "The NIST Definition of Cloud Computing—Recommendations of the National Institute of Standards and Technology"; US Department of Commerce, National Institute of Standards and Technology; Sep. 2011; 7 pages.

* cited by examiner

COGNITIVE SYSTEMS FOR ALLOCATING MEDICAL DATA ACCESS PERMISSIONS USING HISTORICAL CORRELATIONS

BACKGROUND

The present invention generally relates to systems for processing medical data research requests, and more specifically, to cognitive systems for allocating medical data access permissions using historical correlations.

The process of receiving medical data for research is often slow and riddled with error. To get medical data, a medical researcher often needs to write up a data request, either manually or in electronic form, and submit it to an institution's internal review board (IRB) for approval. The IRB then reviews the data request and after upwards of a month, either approves or denies the request. Upon approval, the request is submitted to a server to retrieve the data and/or send to the institution's data administrator (or an individual with similar data provisioning responsibilities) who then manually locates the data to which he thinks the request refers. This data is collected by the data administrator, and/or server, then given to the requestor. If, however, the requestor comes to realize that additional data is needed for the requestor's research, the requestor would need to re-submit a data request to the IRB and repeat the process.

SUMMARY

Embodiments of the present invention provide a computer-implemented method for allocating medical data access permissions using historical correlations. A non-limiting example of the method includes receiving, by a computing system comprising one or more processor, a request for first medical research data from a first user. The method includes executing, by the computing system, natural language processing to interpret the received request. The method includes generating, by the computing system, a database query based on a trained model to identify a first medical research data set that is responsive to the request. The trained model takes into consideration results of the natural language processing of the received request and prior medical research data requests and responses that are stored in a historical database. The method includes querying, by the computing system, one or more medical databases using the generated query to identify the first medical research data set that is responsive to the request. The first medical research data set that is identified by the querying of the one or more medical databases includes the first medical research data and second medical research data that is identified by the computing system as being relevant to the request based on the trained model, in which the second medical research data was not requested by the first user in the request. The method includes transmitting, by the computing system, the first medical research data set to the first user. The method includes logging, by the computing system, the request and the first medical research data set into an audit log.

Embodiments of the present invention provide a system for allocating medical data access permissions using historical correlations. The system includes one or more processors configured to perform a method. A non-limiting example of the method includes receiving, by the system, a request for first medical research data from a first user. The method includes executing, by the system, natural language processing to interpret the received request. The method includes generating, by the system, a database query based on a trained model to identify a first medical research data set that is responsive to the request. The trained model takes into consideration results of the natural language processing of the received request and prior medical research data requests and responses that are stored in a historical database. The method includes querying, by the computing system, one or more medical databases using the generated query to identify the first medical research data set that is responsive to the request. The first medical research data set that is identified by the querying of the one or more medical databases includes the first medical research data and second medical research data that is identified by the computing system as being relevant to the request based on the trained model, in which the second medical research data was not requested by the first user in the request. The method includes transmitting, by the computing system, the first medical research data set to the first user. The method includes logging, by the system, the request and the first medical research data set into an audit log.

Embodiments of the invention provide a computer program product for allocating medical data access permissions using historical correlations, the computer program product comprising a computer readable storage medium having program instructions embodied therewith. The program instructions are executable by a system comprising one or more processors to cause the system to perform a method. A non-limiting example of the method includes receiving, by the system, a request for first medical research data from a first user. The method includes executing, by the system, natural language processing to interpret the received request. The method includes generating, by the system, a database query based on a trained model to identify a first medical research data set that is responsive to the request. The trained model takes into consideration results of the natural language processing of the received request and prior medical research data requests and responses that are stored in a historical database. The method includes querying, by the computing system, one or more medical databases using the generated query to identify the first medical research data set that is responsive to the request. The first medical research data set that is identified by the querying of the one or more medical databases includes the first medical research data and second medical research data that is identified by the computing system as being relevant to the request based on the trained model, in which the second medical research data was not requested by the first user in the request. The method includes transmitting, by the computing system, the first medical research data set to the first user. The method includes logging, by the system, the request and the first medical research data set into an audit log.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, a process, a method, an article, or an apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
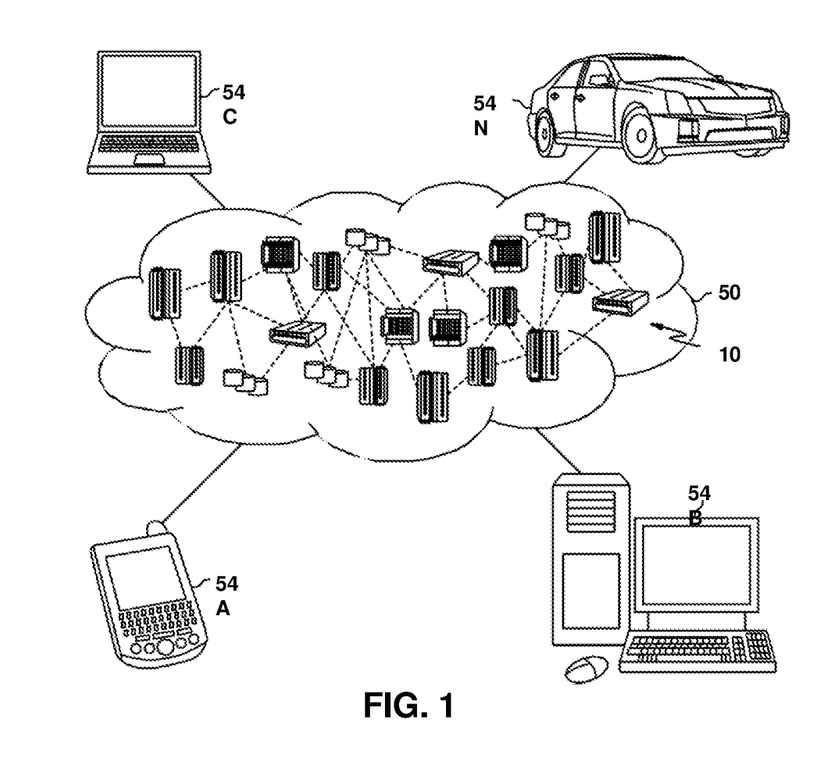
FIG. 1 depicts a cloud computing environment according to one or more embodiments of the present invention.

Referring now to FIG. 1, illustrative cloud computing environment 50 is depicted. As shown, cloud computing environment 50 includes one or more cloud computing nodes 10 with which local computing devices used by cloud consumers, such as for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
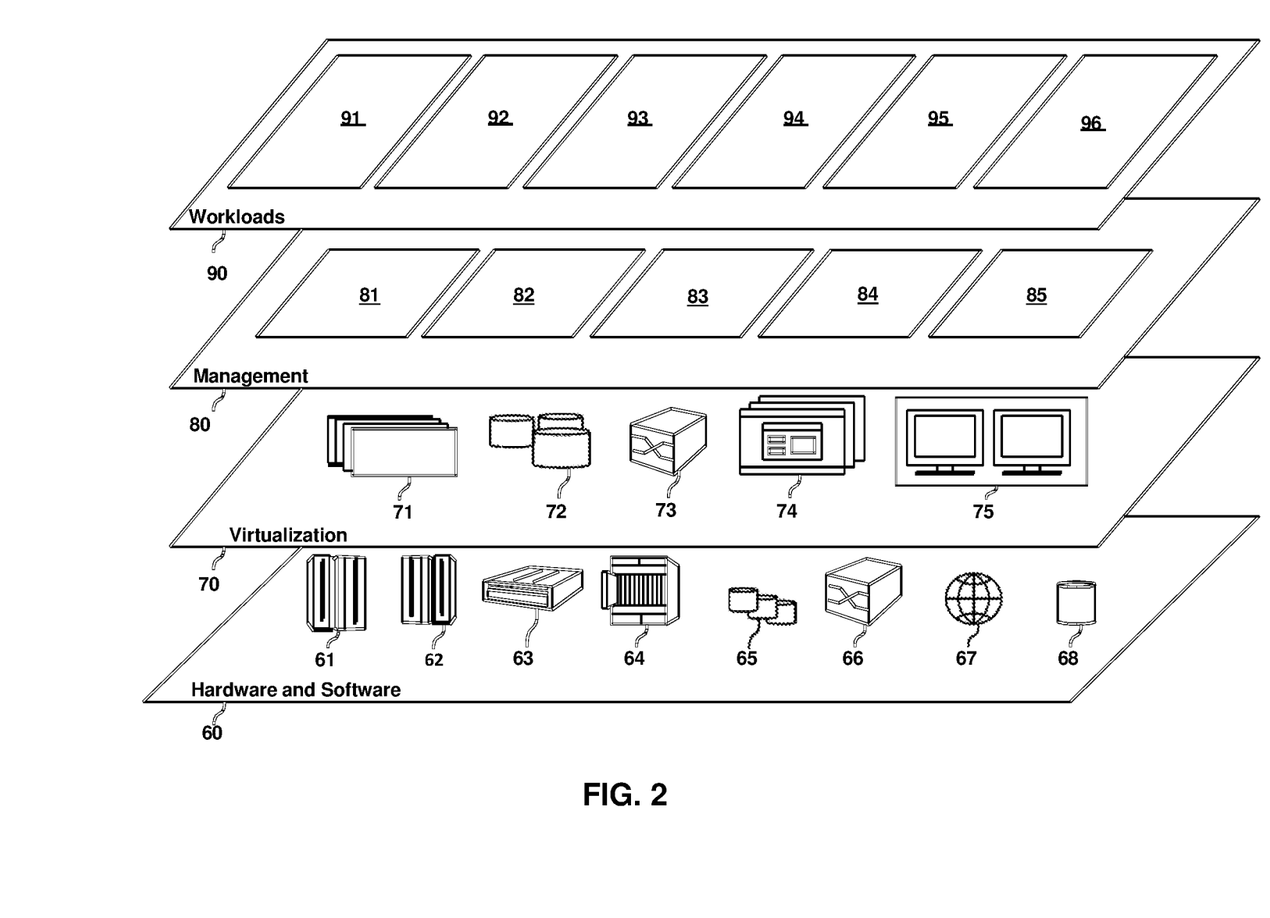
FIG. 2 depicts abstraction model layers according to one or more embodiments of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and medical research data processing 96.

Turning now to an overview of technologies that are more specifically relevant to aspects of the invention, as noted above, the process of receiving medical data for research is often slow and riddled with error. If a requestor who receives a first set of medical research data in response to a submission of a first request, comes to realize that a second set of medical research data is needed for the requestor's research, the requestor would need to re-submit a data request to the IRB and repeat the time consuming and error prone process.

Turning now to an overview of the aspects of the invention, one or more embodiments of the invention addresses the above-described shortcomings of the prior art by providing a cognitive-based system that is capable of using an institution's metadata from historical data request quarries and resulting action of requests to train a machine learning model based on correlations that are identified between the historical data request queries and the resulting actions. Once trained, the machine learning model can be used to identify a dataset to be allocated to a requestor in response to a future request, in which the data set may include data that was not specifically requested by the requestor but identified as potentially being relevant based on the trained machine learning model.

Figure 3:
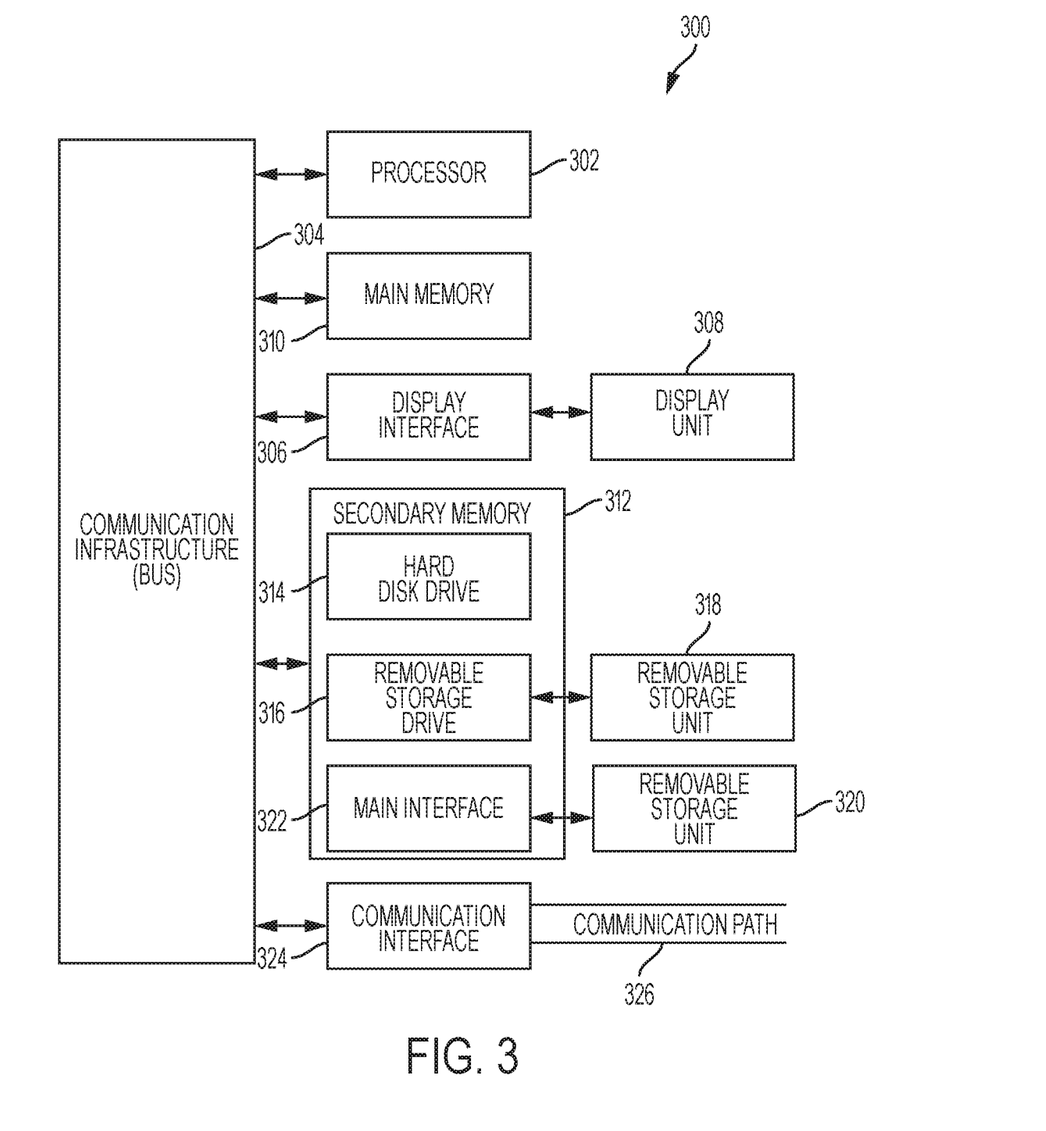
FIG. 3 depicts an exemplary computer system capable of implementing one or more embodiments of the present invention.

Turning now to a more detailed description of aspects of the present invention, FIG. 3 illustrates a high-level block diagram showing an example of a computer-based system 300 useful for implementing one or more embodiments of the invention. Although one exemplary computer system 300 is shown, computer system 300 includes a communication path 326, which connects computer system 300 to additional systems and may include one or more wide area networks (WANs) and/or local area networks (LANs) such as the internet, intranet(s), and/or wireless communication network(s). Computer system 300 and additional systems are in communication via communication path 326, (e.g., to communicate data between them).

Computer system 300 includes one or more processors, such as processor 302. Processor 302 is connected to a communication infrastructure 304 (e.g., a communications bus, cross-over bar, or network). Computer system 300 can include a display interface 306 that forwards graphics, text, and other data from communication infrastructure 304 (or from a frame buffer not shown) for display on a display unit 308. Computer system 300 also includes a main memory 310, preferably random access memory (RAM), and may also include a secondary memory 312. Secondary memory 312 may include, for example, a hard disk drive 314 and/or a removable storage drive 316, representing, for example, a floppy disk drive, a magnetic tape drive, or an optical disk drive. Removable storage drive 316 reads from and/or writes to a removable storage unit 318 in a manner well known to those having ordinary skill in the art. Removable storage unit 318 represents, for example, a floppy disk, a compact disc, a magnetic tape, or an optical disk, etc. which is read by and written to by removable storage drive 316. As will be appreciated, removable storage unit 318 includes a computer readable medium having stored therein computer software and/or data.

In some alternative embodiments of the invention, secondary memory 312 may include other similar means for allowing computer programs or other instructions to be loaded into the computer system. Such means may include, for example, a removable storage unit 320 and an interface 322. Examples of such means may include a program package and package interface (such as that found in video game devices), a removable memory chip (such as an EPROM or PROM) and associated socket, and other removable storage units 320 and interfaces 322 which allow software and data to be transferred from the removable storage unit 320 to computer system 300.

Computer system 300 may also include a communications interface 324. Communications interface 324 allows software and data to be transferred between the computer system and external devices. Examples of communications interface 324 may include a modem, a network interface (such as an Ethernet card), a communications port, or a PCM-CIA slot and card, etcetera. Software and data transferred via communications interface 324 are in the form of signals which may be, for example, electronic, electromagnetic, optical, or other signals capable of being received by communications interface 324. These signals are provided to communications interface 324 via communication path (i.e., channel) 326. Communication path 326 carries signals and may be implemented using wire or cable, fiber optics, a phone line, a cellular phone link, an RF link, and/or other communications channels.

In the present disclosure, the terms "computer program medium," "computer usable medium," and "computer readable medium" are used to generally refer to media such as main memory 310 and secondary memory 312, removable storage drive 316, and a hard disk installed in hard disk drive 314. Computer programs (also called computer control logic) are stored in main memory 310, and/or secondary memory 312. Computer programs may also be received via communications interface 324. Such computer programs, when run, enable the computer system to perform the features of the present disclosure as discussed herein. In particular, the computer programs, when run, enable processor 302 to perform the features of the computer system. Accordingly, such computer programs represent controllers of the computer system.

Figure 4:
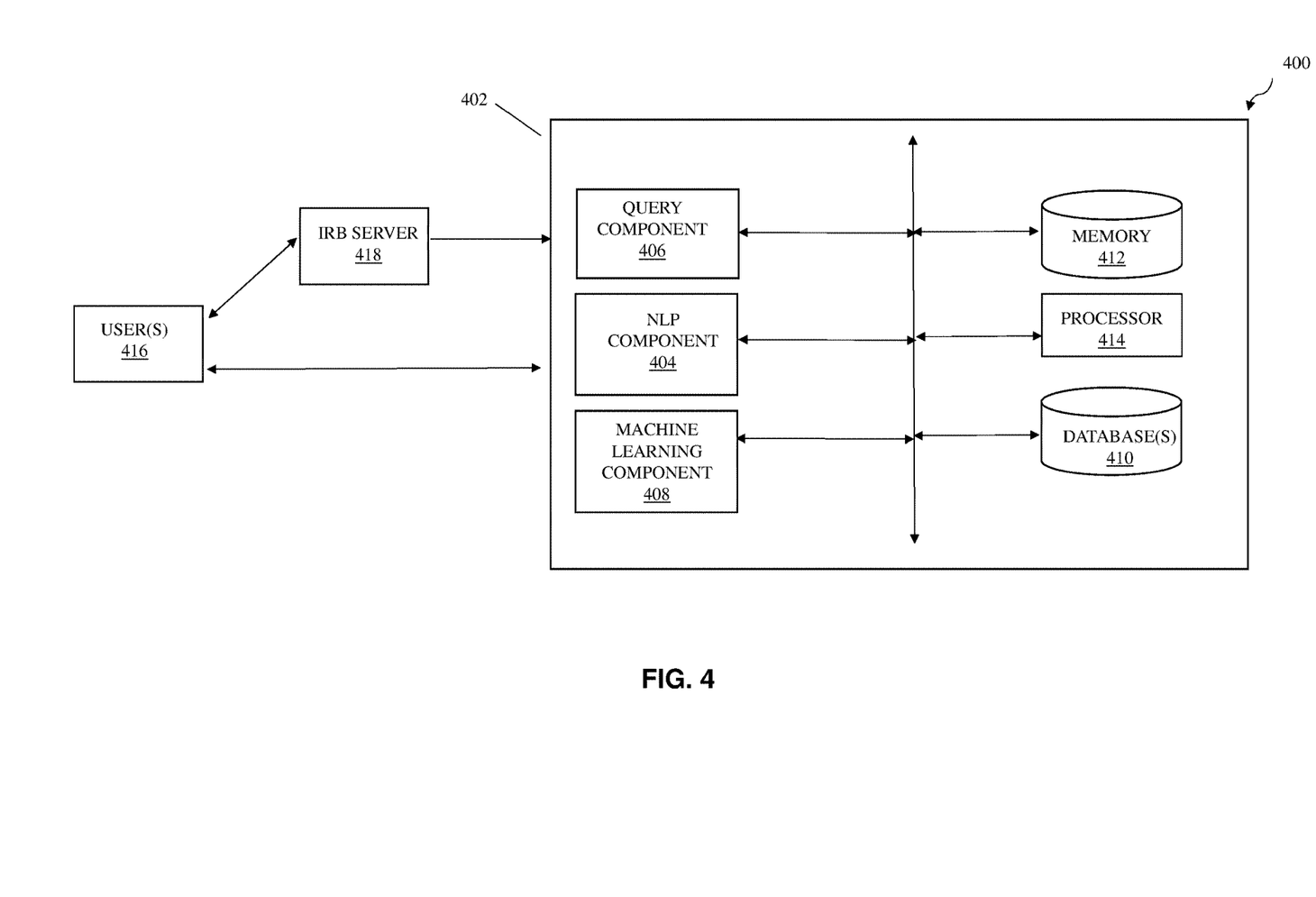
FIG. 4 depicts an exemplary system that allocates medical data access permissions using historical correlations in accordance with one or more embodiments of the present invention.

FIG. 4 depicts an example computer system 400 that is capable of implementing one or more embodiments of the present invention in accordance with one or more embodiments of the present invention. System 400 is a machine learning system that can be utilized to solve a variety of technical issues (e.g., learning previously unknown functional relationships) in connection with technologies such as, but not limited to, machine learning technologies, medical research data processing and permission technologies, data analytics technologies, data classification technologies, data clustering technologies, recommendation system technologies, signal processing technologies, manufacturing defect and analysis technologies, and/or other digital technologies. System 400 employs hardware and/or software to solve problems that are highly technical in nature, that are not abstract and that cannot be performed as a set of mental acts by a human.

The phrase "machine learning" broadly describes a function of an electronic system that learns from data. A machine learning system, engine, or module can include a trainable machine learning algorithm that can be trained, such as in an external cloud environment, to learn currently unknown functional relationships between inputs and outputs.

Machine learning functionality can be implemented using an artificial neural network (ANN) that has the capability to be trained to perform a currently unknown function. In machine learning and cognitive science, ANNs are a family of statistical learning models inspired by the biological neural networks of animals, and in particular the brain. ANNs can be used to estimate or approximate systems and functions that depend on a large number of inputs.

ANNs can be embodied as so-called "neuromorphic" systems of interconnected processor elements that act as simulated "neurons" and exchange "messages" between each other in the form of electronic signals. Similar to the so-called "plasticity" of synaptic neurotransmitter connections that carry messages between biological neurons, the connections in ANNs that carry electronic messages between simulated neurons are provided with numeric weights that correspond to the strength or weakness of a given connection. The weights can be adjusted and tuned based at least in part on experience, making ANNs adaptive to inputs and capable of learning. For example, an ANN for handwriting recognition is defined by a set of input neurons that can be activated by the pixels of an input image. After being weighted and transformed by a function determined by the network's designer, the activation of these input neurons is then passed to other downstream neurons, which are often referred to as "hidden" neurons. This process is repeated until an output neuron is activated. The activated output neuron determines which character was read.

In certain embodiments of the invention, some or all of the processes performed by system 400 are performed by one or more specialized computers (e.g., one or more specialized processing units, a specialized computer with text data component, etc.) for carrying out defined tasks related to machine learning. In some embodiments of the invention, system 400 and/or components of the system are employed to solve new problems that arise through advancements in technologies mentioned above.

In the example shown in FIG. 4, system 400 includes a medical research processing component 402 that includes a natural language processing (NLP) component 404, a query component 406, a machine learning component 408, and one or more database(s) 410. In some embodiments of the invention, medical research processing component 402 constitutes machine-executable component(s) embodied within machine(s) (e.g., embodied in one or more computer readable mediums (or media) associated with one or more machines). Such component(s), when executed by the one or more machines, (e.g., computer(s), computing device(s), virtual machine(s), etc.) cause the machine(s) to perform the operations described. In some embodiments of the invention medical research processing component 402 includes a memory 412 that stores computer executable components and instructions. Furthermore, medical research processing component 402 in some embodiments of the invention includes a processor 414 to facilitate execution of the instructions (e.g., computer executable components and corresponding instructions) by the medical research processing component 402. As shown, the NLP component 404, the query component 406, the machine learning component 408, the database(s) 410, the memory 412, and/or the processor 414 are electrically and/or communicatively coupled to one another in one or more embodiments of the invention.

In general, medical research processing component 402 is a cognitive-based tool that is capable of allocating medical data access permissions using historical correlations. In some embodiments of the present invention, the medical research processing component 402 is configured to receive a request for medical research data from one or more users 416 and/or from an IRB server 418 and to return a medical research data set that is responsive to the request via the use of NLP component 404, query component 406, machine learning component 408, database(s) 410, memory 412 and/or processor 414. For example, in some embodiments of the present invention, the medical research processing component 402 is configured to receive a first request for first medical research data from a first user 416, generate a database query based on trained model to identify a first medical research data set that is responsive to the first request, query one or more medical databases (e.g., database (s) 410 and/or external database) using the generated query to identify the first medical research data set, transmit the first medical research data set to the first user 416, and log the request and the first medical research data set into an audit log (e.g., database(s) 410 and/or external database). In some embodiments of the present invention, medical research processing component 402 is executable by or within the IRB server 418 and/or by a computing device that associated with the user 416.

In some embodiments of the present invention, the first user 416 is a medical researcher who is looking to collect medical data for a particular medical research study. In some embodiments of the present invention, the request is first transmitted by the first user 418 to a server of IRB 418 for institution approval, and then, upon the IRB approving the request, the request is forwarded to the medical research processing component 402. In some embodiments of the present invention, the request is transmitted directly from the first user 416 to the medical research processing component 402. In some embodiments of the present invention, the request may be a written request that is transmitted to the IRB server 418 and/or the medical research processing component 402 in an electronic format. In some embodiments of the present invention, the request is accompanied by a security profile that is transmitted to the medical research processing component 402 in an electronic format. Both the request and security profile may be transmitted to the medical research processing component 402 in a variety of suitable electronic formats, such as for example Word document format, text file format, or PDF format.

The NLP component 404 is configured to execute natural language processing on a received request to interpret a received request. In some embodiments of the present invention, the NLP component 404 is configured to extract various features from one or more fields of a submitted request and to output an NLP result that provides an interpretation of the request in the user's particular context. For example, in some embodiments of the present invention, the natural language processing of the received request may result in the identification of who the requestor is, what the requestor is studying, what type of medical research data is being requested, and/or what the requestor plans on doing with the medical research data once received. Other suitable contextual features may be extracted from a received request. In some embodiments of the present invention, the NLP result is based on application of one or more neural networks that are trained by the machine learning component 408, in which the application of the one or more neural networks on the extracted features can be used to identify if the user 416 may need further medical research data (e.g., second medical research data) in addition to the medical data that was requested (e.g., first medical research data).

Query component 406 is configured to generate a database query based on a trained model that can be used when querying a database to identify a medical research data set that is responsive to the request. For example, in some embodiments of the present invention, query component 406 is configured to generate a first database query based on a trained model that can be used when querying a database to identify a first medical research dataset that is responsive to a first received request. In some embodiments of the present invention, the trained model is configured to take into consideration results of the natural language processing of the first received request (e.g., via NLP component 404). In some embodiments of the present invention, the trained model is configured to take into consideration not only results of the natural language processing of the first received request, but also any prior medical research data requests and responses that are stored in one or more historical databases. In some embodiments of the present invention, the one or more historical databases are stored on the medical research processing component 402 (e.g., database(s) 410). In some embodiments of the present invention, the one or more historical databases are external to the medical research processing component 402. In some embodiments of the present invention, the query component 406 is configured to generate the query further based on NLP processing of a security profile that is received by the medical research processing component 402 from the first user. For example, in some embodiments of the present invention, the medical research processing component 402 is configured to receive a security profile pertaining to the first user 416, in which the security profile is received from the IRB server 418 or directly from the first user 416. Natural language processing is then executed to interpret the security profile and the data base query is generated based on, for example, the results of the natural language processing of the received request and the security profile and the prior medical research data requests and responses that are stored in the one or more historical databases.

In some embodiments of the present invention, query component 406 is configured to query one or more medical databases (e.g., database(s) 410) using the generated query to identify within one or more medical databases a medical research data set that is responsive to a received request. For example, in some embodiments of the present invention, query component 406 is configured to query the one or more medical databases using the generated query to identify the first medical research data set that is responsive to the first request. In some embodiments of the present invention, the one or more medical databases are external to the medical research processing component 402. For example, in some embodiments of the present invention, the one or more medical databases are stored at IRB server 418 and/or at a hospital server that is separate from the IRB server 418.

In some embodiments of the present invention, the first medical research data set that is identified by the query component 406 during the querying of the one or more medical database, via the first generated query, includes the first medical research data that was specifically requested by the first user as well as second medical research data that is identified as being relevant to the request based on the trained model but which was not specifically requested by the first user in the first request.

In some embodiments of the present invention, the second medical research data that is identified during the querying of the one or more medical databases is identified based at least in part on utilizing the trained model to score medical files that are stored on the one or more medical databases (e.g., databases(s) 410 and/or external databases) based on likelihood of being relevant to the first generated query, and then identifying one or more medical files in the one or more medical databases that have a score that meets or exceeds a user-defined confidence interval. In some embodiments of the present invention, the user-defined confidence interval is set by the IRB server 418. In some embodiments of the present invention, the second medical research data that is identified during the querying of the one or more medical databases is identified based at least in part on relationships that are established via one or more trained neural network layers.

In some embodiments of the present invention, the user-defined confidence is predetermined based on a level of security concern that is associated with one or more medical files of the one or more medical databases (e.g., databases(s) 410 and/or external databases). For example, in some embodiments of the present invention, the user-defined confidence interval may be set to 0.70 for data that has a low security concern. In some embodiments of the present invention, the user-defined confidence interval may be set to 0.95 for data that is a high security concern, such that the only data that is identified as being highly relevant is returned to the first user. Other suitable confidence scores or ranges of confidence scores may be utilized. The level of security concern may be established by executing natural language processing on a security profile that is received by the medical research processing component 402 from the one or more users 416 and/or from the IRB server 418.

Machine learning component 408 is configured to train one or more machine learning models and/or algorithm by the medical research processing component 402. For example, in some embodiments of the present invention, the machine learning component 408 is configured to train a model such that the trained model is capable of generating a database query based at least in part on results of natural language processing of a received request and prior medical research data requests and responses that are stored in a historical database, and/or capable of scoring each medical file stored on one or more medical databases (e.g., databases (s) 410 and/or external databases) during the querying of the one or more medical databases using a generated query with a likelihood of being relevant to a given query based on the trained model. In some embodiments of the present invention, the model is trained by retrieving prior medical research data requests and responses that are stored in one or more historical databases (e.g., database(s) 410 and/or external databases) and training one or more neural networks based on the prior medical research data requests and responses. The trained one or more neural networks can be used to train one or more statistical models and/or algorithms. In some embodiments of the present invention, the prior medical research data requests and responses include a plurality of prior requests and a plurality of prior database query results. In some embodiments of the present invention, the plurality of prior requests are requests that were sent by a first user. In some embodiments of the present invention, the plurality of prior requests are requests that were sent by one or more users, which may include the first user and/or other users (e.g., user(s) 416). In some embodiments of the present invention, the plurality prior database query results comprise results that were generated by the medical research processing component 402 at an earlier time in response to processing the plurality of prior requests.

The following is a non-limiting example scenario that may occur through the use of medical research processing component 402 in accordance with one or more embodiments of the present invention, in which the medical research processing component 402 processes a query from a user, and then returns a medical research data set that includes the medical research data that was requested as well as medical research data that was not specifically requested, but identified as being relevant to the query. The scenario is provided for illustrative purposes only.

Adam, an oncologist, is studying pediatric brain tumors and is looking to evaluate mechanisms by which tumors spread in pediatric patients. Adam submits a request to IRB server 418 and/or medical research processing component 402, in which Adam requests that he be provided with: (a) copies of brain scans of patients who are under 15 years and who have been found to have brain tumor in at least three scans; (b) patient demographic data for those patients; (c) the dates of the brain scans of those patients; and (d) data regarding the outcomes of those patients. In response to Adam's request, the medical research processing component 402 searches a medical database for (a)-(d), and then identifies, via NLP component 404, query component 406, and/or machine learning component 408, that another oncologist, Bill, who submitted a prior series of requests for a similar study. In the previous series of requests, Bill had requested to be provided with: (e) data regarding patient results of blood tests that had a presence of a specific hormone; and (f) data for patients who have a specific genomic sequence. The medical research processing component 402 scores the medical files pertaining to (a)-(d) and the dataset that includes medical files pertaining to (e)-(f) via a trained model, and detects that the score meets or exceeds a user-defined confidence interval. As such, in response to Adam's request for (a)-(d), the medical research processing component 402 provides Adam with a dataset that includes (a)-(f) rather than returning a dataset that only includes (a)-(d).

Following is a non-limiting example scenario that may occur through the use of medical research processing component 402 in accordance with one or more embodiments of the present invention, in which the medical research processing component 402 trains an initial working model in accordance with one or more embodiments of the present invention. A requestor, such as medical researcher, submits a request to an IRB in which the requestor asks for a first type of medical research data be provided for a medical research project. Upon a server of the IRB approving the request, the request is forwarded to the medical research processing component 402 for processing of the request. The medical research processing component 402 performs a database query operation on one or more medical databases (e.g., database(s) and/or external databases) that returns a dataset of a second type, which is then transmitted to the requestor. Although the requestor believes the second type of data set is helpful for the medical research project, the requestor decides that the second type of dataset does not capture all of the information that the requestor needs. The requestor then resubmits the request to the IRB. The process repeats, and the requestor is returned a third type of dataset from the system in addition to the second type of dataset, which then fulfils the requestor's needs. The sequence above thus includes a requestor asking for a first type of data set, the requestor receiving a second type of dataset, the requestor re-requesting the first type of dataset (or a different type of dataset), and the requestor then receiving a third data set, in which the combination of the second and third data set meets the requestor's original needs. In some embodiments of the present invention, the machine learning component 408 is configured to utilize a plurality of sequences to train an initial model based on identified correlations between the pluralities of sequences such that if a subsequent requestor submits a request for the first type of data, both the second and third type of data set are provided to the requestor in one batch of data. This reduces the need for subsequent requestors to have to send more than one request for a particular medical research project.

In some embodiments of the present invention, the medical research processing component 402 is further configured to receive a second request from a user for third medical research, return a second medical research data set that includes the third medical research data, and update the trained model based on establishing a statistical correlation score between the first and second medical research data sets. For example, in some embodiments of the present invention, the medical research processing component 402 is configured to receive a second request from the first user for third medical research data, execute natural language processing to interpret the second request, generate a second database query based on the trained model, query the one or more medical databases using the second generated query to identify a second medical research data set that includes the third medical research data, transmit the second medical research data set to the first user, establish a statistical correlation score between the first and second medical research data sets, and log the established correlation score in the audit log and update the trained model based on the established correlation score upon the established correlation score exceeding the user-defined confidence interval.

In some embodiments of the present invention, the medical research processing component 402 is configured to update correlations in the audit log and/or update the trained model based on whether recorded instances exist in which a certain data set is allocated to a user and then left unused or not renewed by the user. For example, in some embodiments, the present invention, subsequent to transmitting the second medical research data set to the first user, the medical research processing component 402 determines whether a renewal request for the second medical research data set is received from the first user during a first period of time. Upon determining that a renewal request for the use of the second medical research data set was not received, in some embodiments of the present invention, the medical research processing component 402 is configured to reduce the established correlation score in the audit log and update the trained model based on the reduced correlation score. In some embodiments of the present invention, subsequent to transmitting the second medical research data set to the first user, the medical research processing component 402 determines whether a renewal request for only the first medical research data set was received from the first user during a first period of time. Upon determining that a renewal request for use of only the first medical research data set was received, in some embodiments of the present invention the medical research processing component 402 is configured to reduce the established correlation score in the audit log and update the trained model based on the reduced correlation score. This process is beneficial as the lack of submission of a request for renewal of the second medical research data set may be indicative that the second medical research data might not have been needed by the first user.

In some embodiments of the present invention, the medical research processing component 402 is configured to update correlations in the audit log and/or update the trained model based on whether recorded instances exist in which a certain data set is allocated to a user and then renewed by the user at a later time. For example, in some embodiments, the present invention, subsequent to transmitting the second medical research data set to the first user, the medical research processing component 402 determines whether a renewal request for the second medical research data set is received from the first user during a first period of time. Upon determining that a renewal request for the use of the second medical research data set was received, in some embodiments of the present invention, the medical research processing component 402 is configured to increase the established correlation score in the audit log and update the trained model based on the increased correlation score. In some embodiments of the present invention, subsequent to transmitting the second medical research data set to the first user, the medical research processing component 402 determines whether a renewal request for only the first medical research data set was received from the first user during a first period of time. This process is beneficial as a submission of a request for renewal of the second medical research data set may be indicative that the second medical research data was correctly identified by the medical research processing component 402 as being needed by the first user.

In some embodiments of the present invention, the medical research processing component 402 is configured to update correlations in the audit log and/or update the trained model based changes in trends in subsequent data request sequences. For example, in some embodiments of the present invention, after an initial correlation is logged in the audit log and or used to train an initial model, requests that are received after training of the initial model may be more heavily weighted in comparison to historical data points when correlations are updated in the audit log and/or the trained model. In some embodiments of the present invention, time frames and/or frequencies of user requests are considered by the medical research processing component 402 when updating correlations in the audit log and/or updating the trained model.

In some embodiments of the present invention, the medical research processing component 402 is configured to update correlations in the audit log and/or to update the trained model based on additional factors such as the nature of a requestor's role. For example, elements such as a job title and/or a department that is associated with a given requestor may be taken into consideration by the medical research processing component 402, in some embodiments of the present invention, in furtherance of identifying correlations. Correlations may rise between requestors' departments and the type of data that is being requested. For example, if a first department typically requests a dataset that includes a first type of data and second type of data, a correlation may be logged between the first and second data.

Figure 5:
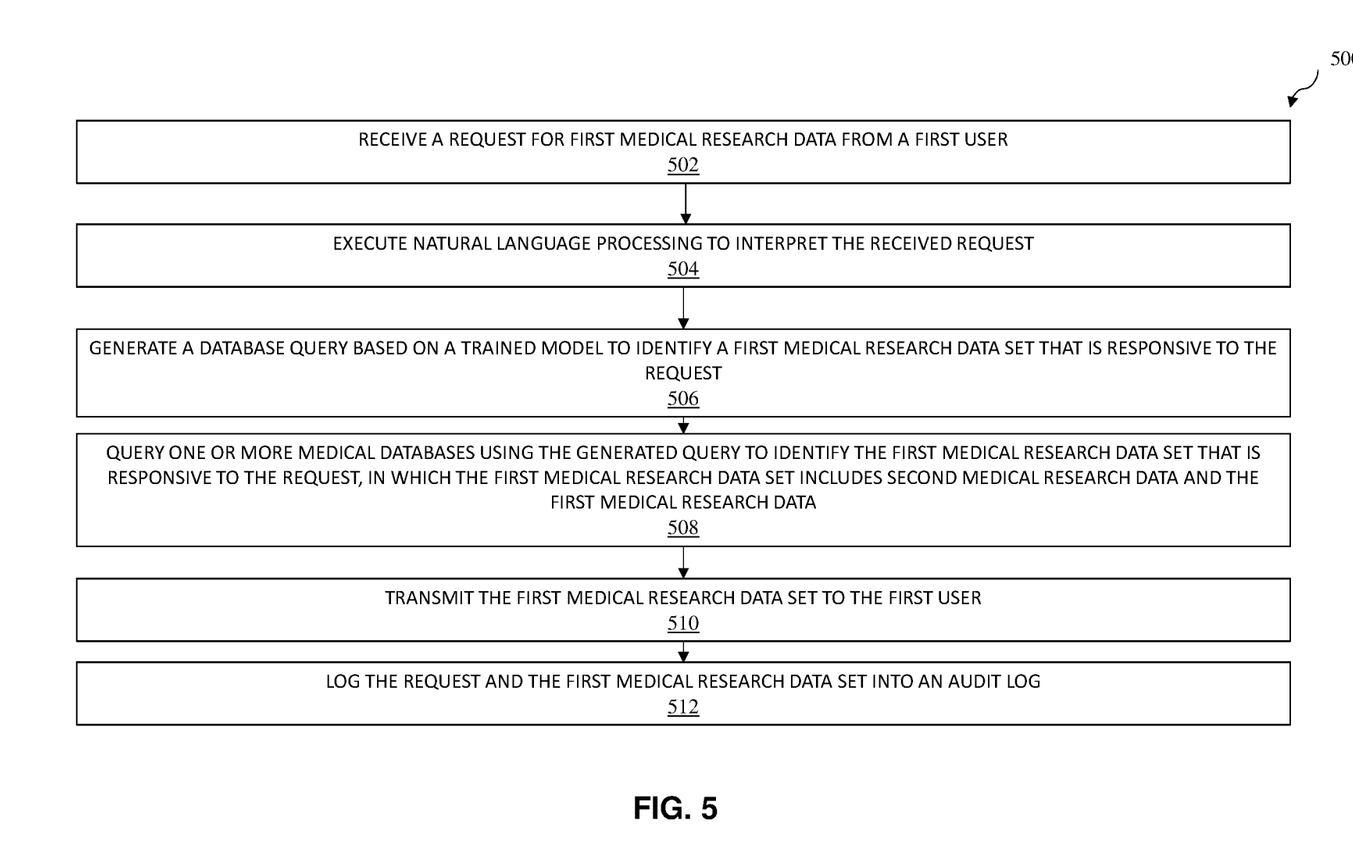
FIG. 5 depicts an example process flow that can be implemented by the system of FIG. 4 in accordance with one or more embodiments the present disclosure.

Additional details of the operation of system 400 will now be described with reference to FIG. 5, which depicts a flow diagram illustrating a methodology 500 according to one or more embodiments of the present invention. At 502, a request for first medical research data is received from a first user. At 504, natural language processing is executed to interpret the received request. At 506, a database query is generated based on a trained model to identify a first medical research data set that is responsive to the request. The trained model takes into consideration results of the natural language processing of the received request and prior medical research data requests and responses that are stored in a historical database. At 508, one or more medical databases are queried using the generated query to identify the first medical research data set that is responsive to the request. The first medical research data set that is identified by the query includes the first medical research data as well as second medical research data that, although not requested by the first user in the request, is identified as being relevant to the request based on the trained model. At 510 the first medical research data set is transmitted to the first user. At 512, the request and the first medical research data set are logged into an audit log.

Figure 6:
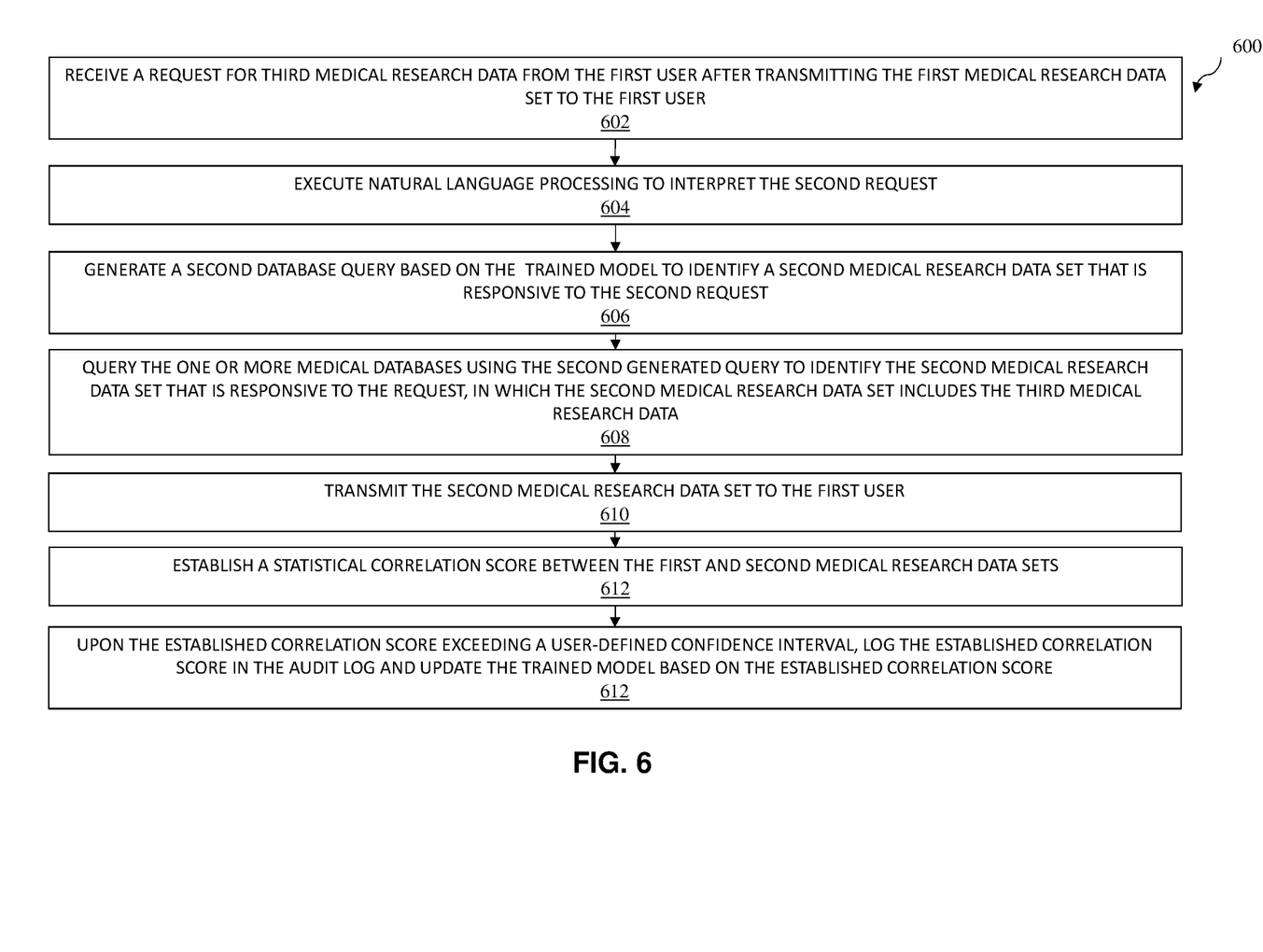
FIG. 6 depicts a further example process flow that can be implemented by the system of FIG. 4 in accordance with one or more embodiments the present disclosure.

FIG. 6, depicts a flow diagram illustrating a methodology 600 in accordance with one or more embodiments of the present invention, in which methodology 600 is utilized subsequent to methodology 500. At 602, a request for third medical research data is received from a first user after transmitting the first medical research data set to the first user. At 604, natural language processing is executed to interpret the second request. At 606, a database query is generated based on the trained model to identify a second medical research data set that is responsive to the second request. The trained model takes into consideration results of the natural language processing of the second request and the prior medical research data requests and responses that are stored in the historical database. At 608, the one or more medical databases are queried using the second generated query to identify the second medical research data set that is responsive to the request. The medical research data set that is identified by the querying of the one or more medical databases includes the third medical research data. At 610 the second medical research data set is transmitted to the first user. At 612, a statistical correlation score is established between the first and second medical research data sets. At 612, upon the established correlation score exceeding or meeting a user-defined confidence interval, the established correlation score is logged in the audit log and the trained model is updated based on the established correlation score.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for allocating medical data access permissions using historical correlations, the computer-implemented method comprising:

receiving, by a computing system comprising one or more processors, a request for first medical research data from a first user;

executing, by the computing system, natural language processing to interpret the request;

generating, by the computing system, a database query based on a trained model to identify a first medical research data set that is responsive to the request, wherein the trained model takes into consideration (a) results of the natural language processing of the received request and (b) prior medical research data requests and responses that are stored in a historical database;

querying, by the computing system, one or more medical databases using the query to identify the first medical research data set that is responsive to the request, wherein the first medical research data set that is identified by the querying includes (a) the first medical research data and (b) second medical research data that is identified by the computing system as being relevant to the request based on the trained model, wherein the second medical research data was not requested by the first user in the request;

transmitting, by the computing system, the first medical research data set to the first user;

logging, by the computing system, the request and the first medical research data set into an audit log; and repeating the receiving, the executing, the generating, the querying, and the transmitting in response to a second request from the first user for third medical research data to identify a second medical research data set that includes the third medical research data;

establishing a statistical correlation score between the first and second medical research data sets; and upon the established correlation score exceeding a user-defined confidence interval, logging the established correlation score in the audit log and updating the trained model based on the established correlation score.

2. The computer-implemented method of claim 1, wherein the model is trained by at least:

retrieving the prior medical research data requests and responses that are stored in the historical database; and training one or more neural networks based on the prior medical research data requests and responses;

wherein the second medical research data that is identified during the querying of the one or more medical databases is identified by at least scoring, during the querying, each medical file stored on the one or more medical databases with a likelihood of being relevant to the query based on the trained model.

3. The computer-implemented method of claim 2, wherein the prior medical research data requests and responses include (a) a plurality of prior requests that were sent from one or more users and (b) a plurality of prior database query results that were generated by the computing system in response to processing of the plurality of prior requests.

4. The computer-implemented method of claim 1, further comprising:
    subsequent to transmitting the second medical research data set to the first user, determining, by the computing system, whether a renewal request for the second medical research data set was received at the computing system from the first user during a first period of time; and
    upon determining that a renewal request for use of the second medical research data set was not received, reducing the established correlation score in the audit log and updating the trained model based on the reduced correlation score.

5. The computer-implemented method of claim 1, wherein prior to receiving the request at the computing system, the request is transmitted from the first user to a server of an internal review board (IRB) of an institution for approval, wherein the request is then received by the computer system from the server of IRB in response to the IRB approving the request via the server.

6. The computer-implemented method of claim 5, further comprising:
    receiving, by the computing system, a security profile pertaining to the first user, wherein the security profiled is received by the computing system from the server of the IRB; and
    executing, by the computing system, natural language processing to interpret the security profile;
    wherein the database query is generated further based on results of the natural language processing of the security profile.

7. A system for allocating medical data access permissions using historical correlations, the system comprising one or more hardware processors configured to perform a method comprising:
    receiving, by the system, a request for first medical research data from a first user;
    executing, by the system, natural language processing to interpret the request;
    generating, by the system, a database query based on a trained model to identify a first medical research data set that is responsive to the request, wherein the trained model takes into consideration (a) results of the natural language processing of the received request and (b) prior medical research data requests and responses that are stored in a historical database;
    querying, by the system, one or more medical databases using the query to identify the first medical research data set that is responsive to the request, wherein the first medical research data set that is identified by the querying of the one or more medical databases includes (a) the first medical research data and (b) second medical research data that is identified by the system as being relevant to the request based on the trained model, wherein the second medical research data was not requested by the first user in the request;
    transmitting, by the system, the first medical research data set to the first user;
    logging, by the system, the request and the first medical research data set into an audit log; and
    repeating the receiving, the executing, the generating, the querying, and the transmitting in response to a second request from the first user for third medical research data to identify a second medical research data set that includes the third medical research data;
    establishing a statistical correlation score between the first and second medical research data sets; and
    upon the established correlation score exceeding a user-defined confidence interval, logging the established correlation score in the audit log and updating the trained model based on the established correlation score.

8. The system of claim 7, wherein the model is trained by at least:
    retrieving the prior medical research data requests and responses that are stored in the historical database; and
    training one or more neural networks based on the prior medical research data requests and responses;
    wherein the second medical research data that is identified during the querying of the one or more medical databases is identified by at least scoring, during the querying, each medical file stored on the one or more medical databases with a likelihood of being relevant to the query based on the trained model.

9. The system of claim 8, wherein the prior medical research data requests and responses include (a) a plurality of prior requests that were sent from one or more users and (b) a plurality of prior database query results that were generated by the system in response to processing of the plurality of prior requests.

10. The system of claim 7, wherein the method further comprises:
    subsequent to transmitting the second medical research data set to the first user, determining, by the system, whether a renewal request for the second medical research data set was received by the system from the first user during a first period of time; and
    upon determining that a renewal request for use of the second medical research data set was not received, reducing the established correlation score in the audit log and updating the trained model based on the reduced correlation score.

11. The system of claim 7, wherein prior to receiving the request at the system, the request is transmitted from the first user to a server of an internal review board (IRB) of an institution for approval, wherein the request is then received by the system from the server of IRB in response to the IRB approving the request via the server.

12. The system of claim 11, wherein the method further comprises:
    receiving, by the system, a security profile pertaining to the first user, wherein the security profiled is received by the system from the server of the IRB; and
    executing, by the system, natural language processing to interpret the security profile;
    wherein the database query is generated further based on results of the natural language processing of the security profile.

13. A computer program product for allocating medical data access permissions using historical correlations, the computer program product comprising a computer readable storage medium having program instructions embodied therewith, the program instructions executable by a system comprising one or more processors to cause the system to perform a method comprising:

receiving, by the system, a request for first medical research data from a first user;

executing, by the system, natural language processing to interpret the received request;

generating, by the system, a database query based on a trained model to identify a first medical research data set that is responsive to the request, wherein the trained model takes into consideration (a) results of the natural language processing of the received request and (b) prior medical research data requests and responses that are stored in a historical database;

querying, by the system, one or more medical databases using the generated query to identify the first medical research data set that is responsive to the request, wherein the first medical research data set that is identified by the querying of the one or more medical databases includes (a) the first medical research data and (b) second medical research data that is identified by the system as being relevant to the request based on the trained model, wherein the second medical research data was not requested by the first user in the request;

transmitting, by the system, the first medical research data set to the first user;

logging, by the system, the request and the first medical research data set into an audit log; and repeating the receiving, the executing, the generating, the querying, and the transmitting in response to a second request from the first user for third medical research data to identify a second medical research data set that includes the third medical research data;

establishing a statistical correlation score between the first and second medical research data sets; and upon the established correlation score exceeding a user-defined confidence interval, logging the established correlation score in the audit log and updating the trained model based on the established correlation score.

14. The computer program product of claim 13, wherein the model is trained by at least:

retrieving the prior medical research data requests and responses that are stored in the historical database; and training one or more neural networks based on the prior medical research data requests and responses;

wherein the second medical research data that is identified during the querying of the one or more medical databases is identified by at least scoring, during the querying, each medical file stored on the one or more medical databases with a likelihood of being relevant to the query based on the trained model.

15. The computer program product of claim 13, wherein the method further comprises:

subsequent to transmitting the second medical research data set to the first user, determining, by the system, whether a renewal request for the second medical research data set was received from the first user during a first period of time; and upon determining that a renewal request for use of the second medical research data set was not received, reducing the established correlation score in the audit log and updating the trained model based on the reduced correlation score.

16. The computer program product of claim 13, wherein prior to receiving the request at the system, the request is transmitted from the first user to a server of an internal review board (IRB) of an institution for approval, wherein the request is then received by the computer from the server of IRB in response to the IRB approving the request via the server.

17. The computer program product of claim 16, wherein the method further comprises:

receiving, by the system, a security profile pertaining to the first user, wherein the security profiled is received by the system from the server of the IRB; and executing, by the system, natural language processing to interpret the security profile;

wherein the database query is generated further based on results of the natural language processing of the security profile.

* * * * *